United States Patent [19]

Baines et al.

[11] 4,343,786

[45] * Aug. 10, 1982

[54] DENTIFRICES CONTAINING ALPHA-ALUMINA TRIHYDRATE

[75] Inventors: Eric Baines, Flixton; John F. Carr, Knutsford, both of England

[73] Assignee: Colgate-Palmolive Company, New York, N.Y.

[*] Notice: The portion of the term of this patent subsequent to Aug. 10, 1999, has been disclaimed.

[21] Appl. No.: 143,067

[22] Filed: Apr. 24, 1980

Related U.S. Application Data

[63] Continuation of Ser. No. 50,935, Jun. 21, 1979, which is a continuation of Ser. No. 871,677, Jan. 23, 1978, which is a continuation of Ser. No. 766,658, Feb. 8, 1977, abandoned, which is a continuation of Ser. No. 640,663, Dec. 15, 1975, abandoned.

[51] Int. Cl.$^3$ .............................................. A61K 7/18
[52] U.S. Cl. ....................................................... 424/52
[58] Field of Search ........................................... 424/52

[56] References Cited

FOREIGN PATENT DOCUMENTS 905301 7/1972 Canada .
911889 10/1972 Canada .
1017676 9/1977 Canada .

*Primary Examiner*—Frank Cacciapaglia, Jr.
*Attorney, Agent, or Firm*—Robert L. Stone; Murray M. Grill; Herbert S. Sylvester

[57] ABSTRACT

Toothpaste containing abrasive particles of milled alpha-alumina trihydrate, alkali metal monofluorophosphate and alkali metal fluoride, the total fluoride corresponding to about 500 to 1000 ppm F, which toothpaste is compatible with an unlined aluminum container and is effective to reduce enamel solubility.

5 Claims, No Drawings

DENTIFRICES CONTAINING ALPHA-ALUMINA TRIHYDRATE

This is a continuation, of application Ser. No. 50,935 filed June 21, 1979, which is a continuation of Ser. No. 871,677, filed Jan. 23, 1978, which is a continuation of 766,658, filed Feb. 8, 1977, now abandoned, which is a continuation of Ser. No. 640,663, filed Dec. 15, 1975, now abandoned.

This invention relates to dentifrices, particularly toothpastes.

Certain aspects of the invention relate to toothpaste formulations containing highly alkaline milled Bayer process alpha-alumina trihydrates. It is found that such toothpaste formulations when packed in unlacquered aluminium tubes react with the aluminium walls of the tube to form gas on storage, even when the pH of the toothpaste is substantially neutral, e.g. 7.1. It has now been found that such reaction on the aluminium walls of the tube may be prevented simply by adjusting the pH of the toothpaste prior to storage to a value in the range of about 5.4 to 6.6 or 6.7, preferably about 5.4 to 6.1 or 6.2. The pH may be adjusted by means of an organic carboxylic acid such as benzoic, citric, tartaric malic, acetic acid, propionic acid or other suitable (e.g. non-toxic) acidic material, such as sodium bisulphate, aluminium fluoride, aluminium sulphate or zinc sulphate.

The highly alkaline milled Bayer process alpha-alumina trihydrate is one which in a 10% slurry in de-ionized water gives a pH of above about 8.5 (such as about 8.8 or more). When used in toothpaste formulation A, set forth below, it may yield a toothpaste having an initial pH (before storage) of at least about 6.9. At such pd or higher (e.g. initial of pH 7.1 or 7.3) the resulting toothpaste, when packed in an unlined aluminium tube, gives visible gas formation accompanied by bloating of the tube on storage at 100° F. (38° C.) for 3 months.

| TOOTHPASTE FORMULATION A | |
|---|---|
| Milled alpha-alumina trihydrate | 55% |
| 70% aqueous solution of sorbitol | 27% |
| Sodium carboxymethyl cellulose | 0.8% |
| Sodium lauryl sulphate | 1.5% |
| Titanium dioxide | 0.5% |
| Saccharin | 0.2% |
| Benzoic acid | 0.15% |
| Flavour | 1.0% |
| Water | Balance |

All proportions herein are by weight unless otherwise indicated.

The foregoing formulation may be made in a conventional manner as by mixing the humectant (sorbitol), gelling agent (dentifrice grade sodium carboxymethyl cellulose) and water, adding saccharin, benzoic acid and flavour, then adding the abrasive (alpha-alumina trihydrate), including the finely divided titanium dioxide whitener, deaerating, and mixing in the detergent (sodium lauryl sulphate). Thus a pre-mix of the sodium carboxymethyl cellulose, benzoic acid, titanium dioxide and saccharin may be prepared, then added to the aqueous sorbitol with agitation, mixed thoroughly with high agitation for 15 minutes, after which the water is added and the mixing is continued for another 15 minutes or more until a smooth lump-free dispersion is obtained; the resulting blend is placed in a vacuum mixing vessel and the alumina trihydrate is drawn into the blend under vacuum while mixing slowly, then the degree of vacuum is increased and mixing at high speed is carried out under the high vacuum for 30 minutes, after which the vacuum is broken, the sodium lauryl sulfate (in solution in water) is added, the high vacuum is restored and the mixing is continued for another 10 minutes; the same procedure as used for the addition and blending of sodium lauryl sulfate is then used for the incorporation of the flavor.

Alkaline alpha-alumina trihydrates which cause corrosion at neutral pH are described, for instance, at page 1 of German OS No. 2509399 published Sept. 11, 1975.

One particular highly alkaline milled Bayer process material is the material made by Baco (British Aluminium Company) and sold under the designation AF 260. A typical sample of this material showed a pH of about 9.5 when dispersed in water at 20% concentration. When a typical sample of this material was incorporated into the previously mentioned toothpaste formulation A but without the 0.15% benzoic acid it was found that the initial pH of the formulation was about 8.1. When this same material was incorporated into that toothpaste formulation A containing the 0.15% benzoic acid, the initial pH of the formulation was about 7.3; on storage for three months at 110° F. (43° C.) considerable gassing occurred. When the total amount of benzoic acid in the formulation was increased to 0.26% the initial pH of the formulation was about 6.3; on storage for 3 months at 110° F. (43° C.) no gassing was observed.

The highly alkaline milled alpha-alumina trihydrate generally has an average particle size in the range of about 2 to about 15 microns. Typically it has a relatively large proportion (such as 40% or 50% or more) of particles smaller than 7.9 microns and may have a low fines content, such as not more than 20% by weight smaller than 3 microns. Thus, one sample of Baco AF260 has the following typical approximate particle size distribution (measured by Coulter counter) 20% finer than 5 microns, 40% finer than 7.5 microns, 58% finer than 10 microns, 82% finer than 15 microns, 91% finer than 20 microns, with a mean particle size of 8 microns, and at most 0.1% retained on a BSS 350 45 microns) sieve. A typical chemical analysis of the Baco AF 260 material is 65.5±0.5% $Al_2O_3$, 34.5±0.5% lost on ignition at 1150° C., 50 ppm maximum heavy metals calculated as Pb, 5 ppm maximum Pb, 1 ppm maximum arsenic, 0.35% $Na_2O$.

In measuring the pH of a slurry of the milled alphaalumina trihydrate the mixture of the solid and de-ionized water is stirred for 5 minutes and then a conventional pH meter is introduced while stirring is continued to maintain a substantially uniform slurry. The measuring instrument may be, for instance, an EIL model 1150 combination pH electrode connected to an Orion model 801 digital pH/mV meter; this may also be employed for measuring the pH values of the toothpastes.

Another aspect of the invention relates to toothpaste formulations containing the highly alkaline milled alphaalumina trihydrate in admixture with sodium fluoride. It is found that such inclusion of sodium fluoride in the toothpaste results in a chemical reaction which raises the pH. For instance, when 0.24% by weight of sodium fluoride was incorporated into a toothpaste containing 0.2% benzoic acid (ordinarily sufficient to give a toothpaste pH of less than about 7, as indicated above) the pH of the toothpaste was found to be about 8.2. The addition of more benzoic acid (e.g. to raise the benzoic acid content to 0.50% giving a pH of 6.20) did not overcome the tendency to react with the tube walls; considerable gassing occurred on storage as described above. It is found, however, that when the fluoride content is supplied by a mixture of sodium monofluorophosphate ("MFP") and sodium fluoride, in a MFP:NaF mol ratio of more than 1:1 the reactive tendency is inhibited. The MFP:NaF mol ratio is preferably at least about 1.5:1 and less than about 10:1, such as about 2:1, 3:1, 4:1, 5:1, 6:1, 7:1, 8:1 or 9:1. The total proportion of soluble fluoride (e.g. MFP calculated as F plus NaF calculated as P) added to the toothpaste is preferably no more than about 1500 ppm, and at least about 500 ppm, most preferably in the range of about 800 to 1100 ppm, e.g. about 1000 ppm.

It is also found unexpectedly that in these MFP-NaF formulations the use of the highly alkaline milled alpha alumina trihydrate results in greater retention of soluble fluoride than when less alkaline milled alpha alumina trihydrate is employed, at the same initial pH of the toothpaste.

Furthermore, use of such formulations permits the solubility of dental enamel to be substantially reduced, particularly as compared to a formulation containing complex fluoride (e.g. MFP as the only source of fluoride. Thus, enamel solubility is reduced compared with the situation in which MFP is the sole fluoride source; while avoiding gassing normally occurring in formulations containing alkali metal fluoride as the sole fluoride source. The following Examples illustrate the use of blends of MFP and NaF.

EXAMPLE 1

A toothpaste formulation is prepared in a conventional manner by mixing the following ingredients: glycerol 20.2%; sodium carboxymethyl cellulose 1.1%, saccharin 0.2%, benzoic acid 0.29%, Baco AF 260 51.5%, titanium dioxide 0.5%, sodium monofluorophosphate (a technical grade containing about 94% sodium monofluorophosphate, together with hydrolysis products thereof such as NaF, phosphates, etc.) 0.82% (about 1000 ppm F): sodium fluoride 0.12% (about 500 ppm F); sodium lauryl sulphate 1.5%, flavour 0.8%; balance water. The initial pH of the toothpaste is 6.7. On storage in unlined aluminium tubes for 3 months at 110° F. (43° C.) it shows a very good fluoride retention and the tubes are not swollen.

EXAMPLES 2-6

Example 1 is repeated except that the proportions of MFP, NaF and benzoic acid, and the initial pH, are as follows:

|  | MFP ppm F | NaF ppm F | Mol Ratio | Initial pH | % Benzoic Acid |
|---|---|---|---|---|---|
| Example 2 | 900 | 100 | 9:1 | 6.7 | 0.250 |
| Example 3 | 860 | 200 | 4:1 | 6.3 | 0.313 |
| Example 4 | 700 | 300 | 2.33:1 | 6.5 | 0.317 |
| Example 5 | 600 | 400 | 1.5:1 | 6.3 | 0.380 |
| Example 6 | 0 | 1000 | 0 | 6.2 | 0.50 |

In each of Examples 2 to 5 the storage (as in Example 1) does not result in gassing and the soluble fluoride content after such storage is measured at over 700 ppm. In the comparison Example 6, the tubes gas severely on such storage and the measured soluble fluoride content is markedly lower.

From the foregoing it will be observed that the use of sodium fluoride in the toothpaste containing alpha-alumina trihydrate of high alkalinity tends to cause attack of unlined aluminum tubes even when the initial pH of the toothpaste is such that attack would be inhibited in the absence of the sodium fluoride. When the proportion of sodium fluoride is such as to provide about 500 ppm F (as in Example 1) but the proportion of MFP is lower than that in Example 1 (i.e. a proposition such as to provide about 500 ppm F, rather than the 1000 ppm F of Example 1) the results have been borderline; thus in two experiments (using the same formulation, except as noted below) in which the molar ratio was 1:1, specifically using amounts of MFP and NaF which each provided 500 ppm F (for a total of 1000 ppm F as in Examples 2 to 6), no gassing was observed when the amount of benzoic acid was 0.40% and the initial pH was 6.6 while severe gassing was observed (under the same 43° C. 3-month storage conditions) when the amount of benzoic acid was 0.33% and the initial pH was 6.4.

As a further aspect of this invention it has been found, quite unexpectedly, that when the toothpaste contains a detergent comprising a carboxylic acid having a long aliphatic hydrocarbon chain attached to the carboxyl through an amide linkage, in place of the sulfoxy detergent, the attack on the unlined aluminum tube is inhibited even when the sodium fluoride is used as the sole source of fluoride and is present in relatively large amounts. The use of this detergent is illustrated in Examples 7–10 below.

EXAMPLES 7–10

Example 1 is repeated except that the 1.5% sodium lauryl sulfate is replaced by 2% sodium N-lauroyl sarcosinate and the proportions of MFP, NaF and benzoic acid, and the initial pH, NaF and benzoic acid, and the initial pH, are as follows:

|  | MFP ppmF | NaF ppmF | Initial pH | % Benzoic Acid |
|---|---|---|---|---|
| Example 7 | 500 | 500 | 6.5 | 0.40 |
| Example 8 | 0 | 1000 | 6.8 | 0.50 |
| Example 9 | 1000 | 500 | — | 0.33 |
| Example 10 | 0 | 1500 | 6.3 | 0.80 |

In each of Examples 7 to 10 the storage (as in Example 1) does not result in gassing, and measurements of soluble fluoride after such storage indicate good fluoride retention.

It is also found that the use of the detergent which is a fatty acid interrupted by an amide linkage, in place of the sulfoxy detergent, also has a beneficial effect when the alphaalumina trihydrate is of a less alkaline type. One example of such a material is Alcoa C-333 a product of Alcoa (Aluminium Company of America). Its specifications state that its average particle size is about 6.5–8.5 microns and, by hydrometer analysis, 94–99% is below 30 microns, 85–93% is below 20 microns, 56–67% is below 10 microns and 28–40% is below 5 microns. Other typical properties as given by the manufacturer are $Al_2O_3$ 65.0% (64.5% minimum), $SiO_2$ 0.01% (0.02% maximum), $Fe_2O_3$ 0.005% (0.005% maximum), $Na_2O$ 0.15% (0.25% maximum), soluble $Na_2O$ (by standard Alcoa test methods) 0.02% (0.04% maximum), moisture (110° C.) 0.4% (0.70% maximum), bulk density (loose) 44 lb/ft$^3$, bulk density (packed) 77 lb/ft$^3$, specific gravity 2.42, screen analysis 99% through 325 mesh sieve (58% minimum). Its pH, measured in a 20% slurry in deionized water is usually about 8.5 or less. When this material is employed in toothpaste formulation A, given above, it typically yields a toothpaste having an initial pH well below 6.7, such as about 6.2. Examples 11 to 14 below relate to this aspect of the invention.

EXAMPLES 11–14

Example 1 is repeated except that the 51.5% Baco AF-260 and 0.5% titanium dioxide are replaced by 52% Alcoa C-333, the 1.5% sodium lauryl sulfate is replaced (in Examples 11 and 12) by 2% sodium N-lauroyl sarcosinate and the proportions of MFP, NaF and benzoic acid, and the initial pH, are as follows:

|  | MFP ppmF | NaF ppmF | Initial pH | % Benzoic Acid |
|---|---|---|---|---|
| Example 11 | 0 | 1500 | 6.3 | 0.833 |
| Example 12 | 500 | 500 | 6.8 | 0.40 |
| Example 13 (sodium lauryl sulfate) | 0 | 1000 | 6.4 | 0.50 |
| Example 14 (sodium lauryl sulfate) | 0 | 1000 | 6.5 | 0.63 |

Storage (as in Example 1) does not result in gassing for Examples 11 and 12 (containing the N-lauroyl sarcosine) but results in severe gassing for Examples 13 and 14.

With respect to the fluoride retention on such storage it is significantly better when the more alkaline grade (of Examples 1 to 10) is used than when the less alkaline grade (of Examples 11 to 14) is employed.

In these Examples the fluoride compounds are included, as dry powders, in the pre-mix (with benzoic acid) as mentioned above. They may be added in other ways, as in the aqueous solution of the detergent which is incorporated after the alumina trihydrate has been added.

It will be noted that the Baco trihydrate, which appears to be somewhat less reactive with the fluoride, has a lower fines content than the Alcoa trihydrate and thus may have a smaller surface area for reaction. The manufacturer of Baco AF-260 has advised that its surface area (as measured by light extinction) is well below 1.5 m$^2$/g, specifically about 1.0-m$^2$/g e.g. 1.1 m$^2$/g. The manufacturer of Alcoa C-333 has advised that its surface area (as measured by BET nitrogen adsorption) is about 2–2.5 m$^2$/g. The light extinction method for measuring specific surface is described at pages 10–12 of the publication "The Physical Examination of Alumina" published by B.A. Chemicals Ltd., London, which teaches that the method correlates well with other procedures.

Another aspect of the invention relates to milled alpha alumina trihydrate which has been modified during its manufacture.

A conventional way of manufacturing alpha alumina trihydrate (herein referred to simply as "trihydrate") is by the Bayer process. In that process trihydrate is precipitated from a solution of sodium aluminate. See Encyclopedia of Chemical Technology, Kirk-Othmer, 2nd Edition, Vol. 1, p. 937–941 and Vol. 2, p. 41–45, 50–51. The trihydrate is precipitated in the form of granules or agglomerates which are too large for general use as a dentifrice abrasive, e.g. about 40–100 microns diameter. Therefore, the granules or agglomerates after drying (sometimes after water-washing and drying) are ground to a suitable particle size, e.g. to an average particle diameter in the range of about 2 to 20 microns, such as about 5 to 10 microns diameter.

The washed, unground granules show an alkaline reaction when slurried in water. For instance, depending on the degree of washing before drying, the pH of a 10% or 20% by weight of trihydrate slurry at room temperature may be in the range of about 7.5 to 8.5, 9 or 9.5.

The pH can be measured with an Orion model 801 Digital ph/mv meter which is filled with an EIL model 1150 Combination pH and reference electrode. The instrument is first calibrated at room temperature by placing the electrode into 50 ml. of pH buffer solution in a 100 ml. beaker, and adjusting the calibration control until the instrument reading corresponds to the buffer pH. The electrode is then removed, washed with deionised water, and placed into 125 gms. of a prepared 20% slurry of the trihydrate sample in deionized water in a 250 ml. beaker, and its pH reading taken.

On grinding, the alkalinity, thus measured, increases and the pH measured (as above) of the ground, unwashed, material is generally above about 8. For instance the pH on grinding may change as follows: 7.5 (before grinding) to 8.8 (after grinding); 8.8 (before) to 9.2 (after).

According to one aspect of the invention a dentifrice comprises an aqueous medium or vehicle and, as an abrasive, ground trihydrate made by the Bayer process, the grinding having been performed in the presence of a surface-modifying agent.

It is believed that by grinding the trihydrate in the presence of a surface modifying agent, inclusions of alkali exposed by fracture of the trihydrate granules during the grinding, or highly active sites produced by fracturing during grinding, may be brought into intimate contact with the surface modifying agent and thereby neutralized or inactivated.

The invention reduces the risk of localized corrosion in the dentifrice during storage.

The amount of surface-modifying agent required will generally be within the range from about 0.01 to 2%, such as about 0.1% or 0.5%, by weight based on the weight of trihydrate.

Surface-modifying agents may act by deactivating reactive sites on the trihydrate and/or forming at least a monomolecular coating on the trihydrate, at least during the beginning of grinding. Surface-modifying agents which may be employed are non-toxic and include organic acids, which contain a polar and non-polar group, and salts thereof, such as benzoic acid, lauric acid, stearic acid, oleic acid, naphthenic acid, fatty acyl amides of the amino acids, such as N-lauroyl (or N-oleoyl or N-stearoyl) sarcosine, phenol and the like which have low water solubility and salts thereof as well as solid or liquid organic acids of greater water-solubility such as acetic acid, propionic acid or other lower alkyl carboxylic acids, citric acid, tartaric acid, malic acid, and salts thereof, such as alkali metal salts, e.g. sodium. Polar-non-polar carboxylic acids and salts are described in U.S. Pat. No. 2,274,521 granted Feb. 24, 1942. Inorganic acid forming salts such as sodium bisulphate and aluminium chloride, aluminium sulphate and zinc sulfate also may be employed.

Additional non-toxic surface-modifying agents which may be employed include mono- and polyhydric alcoholics; dentally acceptable polishing and thickening agents; and polyelectrolytes. The most preferred materials are those which are more acidic than the trihydrate.

Mono- and polyhydric alcohols include methanol, ethanol, n-propanol, isopropanol, n-octanol, ethylene glycol, triethylene glycol, ethylene glycol monomethyl ether, 1-amino-2-propanol, monoethanolamine and triethanolamine.

Dentally acceptable polishing materials which can modify the surface of the trihydrate include insoluble sodium metaphosphate, dicalcium phosphate, calcium carbonate and other alkali earth metal phosphates and carbonates, sodium aluminosilicate and crystalline and colloidal silica. The surface modifying agent may be a material of very fine particle size, e.g. less than 1 micron diameter; acidic silica particles such as pyrogenic silica, e.g. "Cabosil," may be used.

Polyelectrolytes, particularly those ionic polymeric polyelectrolytes available under the name Tamol, such as Tamol 731 and Tamol 850, also can modify the surface of the trihydrate. Polymeric carboxylic acids, such as the vinyl methyl ethermaleic anhydride copolymer, can be used for this purpose.

In addition to the surface modifying agents mentioned above, suitable materials include detergents such as anionic sulphates, and phosphates, nonionic condensates including an ethylene oxide moiety and ampholytics such as imidazole derivatives. Typical detergents are described below.

Non-polar materials including waxes, vegetable oils, such as palm oil and hydrogenated palm oil, and hydrocarbon oils and grease, e.g. mineral oils such as liquid paraffin, e.g. light or heavy petrolatum, petroleum jelly and petroleum wax can also modify the surface of the trihydrate.

It is preferred that the amount of surface-modifying agent present be at least that needed to form a monomolecular coating in the trihydrate particles, as to enter into reaction with and deactivate sites in the trihydrate, at least during the beginning of the grinding; preferably an excess, such as 5% (or more) excess, is used, particularly when ball milling. The surface area of the trihydrate granules before grinding is generally well below 1 m²/g and it may increase during grinding to about 1 m²/g or above, such as 1.1 to 3 or 5 m²/g or higher.

The surface modifying agent may be in liquid form at the ambient grinding temperature. This may be for instance, a solution, a solid surface modifying agent in a solvent therefore, or a liquid mixture of solid and liquid surface modifying agents, such as a 50—50 mixture of ethylene glycol and benzoic acid, mineral oil and stearic acid and mineral oil and benzoic acid. The grinding temperature is generally well below 100° C. such as about 20°, 30° or 40° C. The material being ground is preferably substantially dry, e.g. its water content is preferably below 20% of the weight of trihydrate, such as 1% or 2%.

The grinding of the trihydrate in the presence of the surface modifying agent may be practiced using techniques and apparatus recognised in the art. For instance, ball milling is described in "Surface Activity in Fine Dry Grinding" Berry & Kamack, pages 196-202, in Solid/Liquid Interface; Cell/Water Interface (Biological) Vol. 4. Edited by J. H. Schulman (Proceedings of the Second International Congress on Surface Activity, London, 1957) Academic Press, New York, 1958, "Grinding Low-Soda Alumina" by Hart and Hudson, Ceramic Bulletin, Vol. 43, No. 1 (1964); and U.S. Pat. No. 3,358,937 granted Dec. 19, 1967; Vibrative-Energy Milling is described in the article by Hart & Hudson and Pin-type Milling is described in Perry, Chemical Engineers' Handbook, 5th Edition, 1073, pages 8-37 to 8-71.

The surface-modifying agent may be added to the material being fed to the mill, may be metered into the mill itself during operation or may be added to the wet slurry before grinding. It is also within the broad scope of the invention to add the surface modifying agent to the size classification zone associated with the mill. Thus it is common to pass the product of the mill to a size classification zone (e.g. a cyclone) from which the oversize, insufficiently ground, particles are returned to the mill for further grinding.

EXAMPLE 15

A washed unground Bayer process trihydrate of the more alkaline (Baco) type is ground in the presence of 0.5% benzoic acid and the resulting milled trihydrate is used in a formulation as set forth in Example 1 above. The pH of the toothpaste is about 6.3. On aging at 43° C. for 3 months in unlined aluminium tubes only very slight gassing is observed.

EXAMPLES 16-20

Pulverisation and reduction of particle size of granules of washed Bayer process alumina trihydrate is affected by charging a porcelain ball mill pot containing a 50% ball charge of porcelain balls ranging in diameter from 1 cm to 2.5 cm with the alumina trihydrate granules together with 0.5% benzoic acid based on the weight of the trihydrate such that the ratio of ball volume to powder volume is 2:1. Pot sizes range from 0.5 liter to 30 liter depending on charge size, 1 liter is used.

The pot is sealed, and placed on a No. 2 Motorised Pascall Laboratory Ball Mill such that it rotates horizontally about its axis on a pair of rubber covered rollers, one driven and one idler, each 13¼" long. Drive is by a ¼ H.P. electric motor with a variable speed control. The motor is started and the speed adjusted such that the balls tumble in the mill pot to reduce the particle size of the trihydrate. The motor is then stopped, the pot removed and the charge separated from the balls by sieving and then suitably classified to remove large particles, such as those larger than 20 microns, which large particles are returned to the ball mill.

| Ingredients | Example Number | | | | |
|---|---|---|---|---|---|
| | 16 | 17 | 18 | 19 | 20 |
| Abrasive - Ground Trihydrate prepared as above | 52.0 | 52.0 | 52.0 | 52.0 | 52.0 |
| Humectant | | | | | |
| Glycerine | 20.0 | 20.0 | 20.0 | 15.0 | 20.0 |
| Sorbitol | — | — | — | 5.0 | — |
| Thickener | | | | | |
| Sodium carboxymethyl cellulose | 1.1 | 1.1 | 1.1 | 1.1 | 1.1 |
| Flavour and Sweetener | | | | | |
| Flavour | 0.8 | 0.8 | 0.8 | 0.8 | 0.8 |
| Sodium saccharinate | 0.2 | 0.2 | 0.2 | 0.2 | 0.2 |
| Detergent (Note 2) | | | | | |
| Sodium lauryl sulphate | 1.5 | 1.5 | 1.5 | 1.5 | 1.5 |
| Propylactic agent | | | | | |
| Sodium monofluorophosphate | 0.5 | 0.4 | — | — | — |
| Sodium fluoride | — | 0.1 | 0.2 | — | — |

| Ingredients | Example Number | | | | |
|---|---|---|---|---|---|
| | 16 | 17 | 18 | 19 | 20 |
| Water | 23.9 | 23.9 | 24.2 | 23.9 | 23.9 |

Note 1
In modified Examples the sodium carboxymethyl cellulose is replaced by hydroxyethyl cellulose and by Irish Moss.

Note 2
In other modified Examples the sodium lauryl sulphate is replaced by sodium N-lauroyl sarcosinate.

The toothpastes are packaged in unlined aluminium tubes.

The surface-modifying agents mentioned above may also be incorporated into the toothpaste formulation without first contacting them with the abrasive. One particularly suitable agent for this purpose is pyrogenic silica such as that sold as Aerosil or Cabosil, as illustrated in the Example below:

EXAMPLE 21

A toothpaste is prepared from about 20.2% glycerine, 0.9% sodium carboxymethyl cellulose, 0.2% saccharin, 46% trihydrate (Baco AF-260), 2.5% pyrogenic silica, 1.54% sodium lauroyl sarcosinate, 0.8% flavor and the balance water. The initial pH of the toothpaste is about 7.8. When packed in unlined aluminium tubes it does not corrode or gas on aging for 3 months at 43° C.

The Aerosil 200 is a hydrophilic pyrogenic silica having an acidic reaction. Typically the grade 200 has a BET surface area of $200 \pm 25$ m$^2$/g and a pH (in 4% slurry in water) of about 3.6 to 4.3 Detailed descriptions of this material are found in publications of the manufacturer, Degussa; see for instance Kautschuk und Summi, Kunststaffe 20 (1967) p. 578-586. The Aerosil particles have silanol groups at their surfaces and, in aqueous dispersion, the particles move, under the influence of an electric field, to the positive pole, i.e. they carry a negative charge.

As illustrated above, the toothpastes generally contain an aqueous vehicle including a gelling agent and a detergent or surface-active agent, together with flavor and sweetener, besides the alpha-alumina trihydrate. Other ingredients may be present as well. Naturally those skilled in the art should select such ingredients and in such proportions as not to adversely affect the operability of the formulations for the purpose at hand.

Organic surface-active agents may be used in the dentifrice to achieve increased prophylactic action, assist in achieving thorough and complete dispersion of the compositions throughout the oral cavity, and render the compositions more cosmetically acceptable. It is preferred to employ as the surface-active agent a detersive material which imparts to the dentifrice detersive and foaming properties. The proportion of surface-active agent is generally within the range of about 0.05 to 5% more usually within the range of about 0.5 to 3% such as about 1 to 2%. As indicated above, a particularly preferred surface-active agent or detergent is an N-acyl sarcosine surfactant having at least about 10 carbon atoms (e.g. 12-18 carbon atoms) in the acyl group, such as sodium N-lauroyl sarcosinate. It is also within the scope of the invention to use other amide-linked carboxylic surfactants such higher aliphatic acyl amides of lower aliphatic amino carboxylic acid compounds (such as those having, say 12 to 16 or 18 carbon atoms in the higher acyl radical which is preferably of the saturated type, and up to 4 carbon atoms in the amino carboxylic portion) and including those disclosed at pages 37 to 29 of Schwartz and Perry Surface Active Agents and Detergents Volume II published 1958 by Interscience Publishers. The amide-linked carboxylic surfactant may be substantially the sole surface-active agent; in the broader scope of that aspect of the invention there may also be present other anionic and amphoteric or non-ionic surface-active agents, preferably in minor amounts in relation to the amide-linked surfactant (such as less than about 1% of the total toothpaste formulation, e.g. 0.7% or 0.5%).

The anionic detergents include water-soluble salts of higher (i.e. having at least 12 carbon atoms) fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzone sulphonate, olefin sulphonates, such as sodium olefin sulphonate in which the olefin group contains 12-21 carbon atoms, higher alkyl sulphoacetates, higher fatty acid esters of 1,2-dihydroxy propane sulphonates.

The nonionic surface-active agents include such materials as condensates of sorbitan monostearate with approximately 60 moles of ethylene oxide with propylene oxide condensates of propylene glycol ("Pluronics"—PLURONIC is a Trade Mark), other examples of suitable nonionic detergents are condensation products of alkyl phenols with ethylene oxide, e.g. the reaction product of iso-octyl phenol with 6 to 30 ethylene oxide units; condensation products of alkyl thiophenols with 10 to 15 ethylene oxide units; condensation products of higher fatty alcohols and monoesters of hexahydric alcohols and inner ethers thereof such as sorbitan monolaurate, sorbitol mono-oleate and mannitan monopalmitate.

Examples of amphoteric detergents are N-alkylbetaaminopropionic acid; and N-alkyl-beta imino-dipropionic acid; and N-alkyl, N,N-dimethyl glycine. The alkyl group may be, for example, that derived from coco fatty alcohol, lauryl alcohol, myristyl alcohol (or a lauryl-myristyl mixture), hydrogenated tallow alcohol, cetyl alcohol, stearyl alcohol or blends of such alcohols. The substituted amino-propionic and iminodipropionic acids are often supplied as the sodium or other salt forms, which may likewise be used in the practice of this invention. Examples of other amphoteric detergents are betaines containing a sulphonic group instead of the carboxylic group; betaines in which the long chain substituent is joined to the carboxylic group without an intervening nitrogen atom, e.g. inner salts of 2-trimethylamino fatty acids such as 2-trimethyaminolauric acid, and compounds of any of the previously mentioned types in which the nitrogen atom is replaced by phosphorus.

It is also within the broader scope of the invention to employ a cationic surface-active agent or detergent. Examples of these are diamines such as those of the type

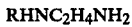

$RHNC_2H_4NH_2$ wherein R is an alkyl group of 12 to 22 carbon atoms such as N-2-aminoethyl stearyl amine and N-2-aminoethyl myristyl amine; amido-linked amines such as those of the type $R^1CONHC_2H_4NH_2$ wherein $R^1$ is an alkyl group of 9 to 20 carbon atoms, such as N-2-amino ethyl-stearyl amide and N-amino ethyl myristyl amide; quaternary ammonium compounds wherein typically one of the groups linked to the nitrogen atom is an alkyl group which contains an alkyl group of 10 to 18 carbon atoms and each of the other alkyl groups typically contains 1 to 3 carbon atoms and which may bear inert substituents such as phenyl groups, and there is present an anion such as halogen, acetate or methosulphate. Typical quaternary ammonium detergents are ethyl-dimethyl-stearyl ammonium chloride, benzyl-dimethyl myristyl ammonium chloride, benzyl-dimethylstearyl ammonium bromide, trimethyl stearyl ammonium chloride, trimethylcetyl ammonium bromide, dimethyl-ethyl dilauryl ammonium chloride, dimethyl-propyl-myristyl ammonium chloride and the corresponding methosulphates and acetates. Other cationic surface active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12–18 carbon atoms) and two (poly) oxyethylene groups attached to the nitrogen (typically containing a total of from 20 to 50 ethanoxy groups per Molecule) and salts thereof with acids, and compounds of the structure.

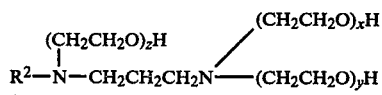

wherein $R^2$ is a fatty alkyl group typically containing from 12 to 18 carbon atoms, and x, y, and z total 3 or higher, as well as salts thereof with mineral or organic acids, may also be used.

The aqueous vehicle of the dentifrice preferably forms, with the abrasive particles, a mass of a consistency which can be extruded from a collapsible aluminium tube. The vehicle will generally contain liquids and solids. In general, the liquid portion comprises water, glycerine or aqueous sorbitol, including suitable mixtures thereof. It is usually advantageous to use a mixture of both water and a humectant such as glycerine or sorbitol. The total liquid content is generally 20–90% by weight of the dentifrice and typically includes up to 30% by weight of water, 0–80% by weight of glycerine and 0–80% by weight of sorbitol. Preferably up to 20% by weight of water, 15–40% by weight of glycerine and 0–50% by weight of sorbitol are present in the dentifrice.

The solid portion of the vehicle may be a gelling agent, such as the natural and synthetic gums and gum-like materials, such as Irish Moss, gum tragacanth, alkali metal carboxymethyl cellulose and hydroxyethyl carboxyl-methyl cellulose, polyvinyl pyrrolidone, starch water soluble, hydrophilic colloidal carboxyvinyl polymers, such as those sold under the trademark Carbopol 934 and 940 and synthetic inorganic silicate clays such as those sold under the trademark Laponite CP and Laponite SP. These grades of Laponite have the formula

The solid portion of the vehicle is typically present in amount up to 10% by weight of the dentifrice and preferably 0.5–5% by weight. When employed, grades of Laponite are preferably used in amount of 1–5% by weight.

Any suitable flavoring or sweetening materials may be employed in formulating a flavor for the dentifrice.

Examples of suitable flavor constituents include flavoring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, perillartine and saccharine. Suitably, flavor and sweetening agents may together constitute from 0.01 to 5% or more of the dentifrice. Chloroform may also be used.

It is also within the scope of the invention (particularly the aspects in which the surface of the trihydrate is modified and/or when a mixture of the monofluorophosphate and fluoride is used) to employ a less alkaline milled alpha-alumina trihydrate in place of part (e.g. ¼, ½ or ¾) or all of the highly alkaline material.

In the broader aspects of the invention, particularly with respect to surface-modified material, the alumina trihydrate need not be the sole abrasive in the dentifrice. Other dental abrasives which may also be present include calcium carbonate, magnesium carbonate, tricalcium phosphate, dicalcium phosphate dihydrate, insoluble sodium metaphosphate, calcium pyrophosphate, synthetic amorphous complex aluminosilicates, silica (including dehydrated silica gel.) The total amount of abrasive including ground trihydrate will usually be in the range from 10 to 60%, preferably 20 to 60% by weight of the dentifrice. The alkali metal monofluorophosphates which may be employed include sodium monofluorophosphate, lithium monofluorophosphate, potassium monofluorophosphate and ammonium monofluorophosphate. The preferred salt is sodium monofluorophosphate, $Na_2PO_3F$, which, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight as sodium monofluorophosphate with the balance being primarily impurities or by products of manufacture such as sodium fluoride and water-soluble sodium phosphate salt. Expressed in another way, the sodium monofluorophosphate typically has a total fluoride content of above 12%, preferably above 12.7%, a content of up to 1.5%, typically up to 1.2% of free sodium fluoride; and a sodium monofluorophosphate content of at least 12%, preferably at least 12.1% all calculated as fluorine. Other monofluorophosphate salts which may be used include monofluorophosphates such as $Na_4P_3O_9F$, $K_4P_3O_9F$, $(NH_4)_4P_3O_9F$, $Na_3KP_3O_9F$, $(NH_4)_3NaP_3O_9F$, and $Li_4P_3O_9F$. In the broader aspects of the invention various other materials may be incorporated in the dentifrices. Examples thereof are coloring or whitening agents or dyestuffs, preservatives, silicones, chlorophyll compounds, ammoniated materials such as urea, diammonium-phosphate and mixtures thereof, antibacterials and other constituents. The adjuvants are incorporated in the compositions in amounts which do not substantially adversely affect the properties and characteristics desired. When antibacterials are present, typically the amount is 0.01–5% by weight. Typical antibacterial agents include $N'$-(4-chlorbenzyl)-$N^5$-(2,4-dichlorobenzyl) biguanide; p-chlorophenyl biguanide; 4-chlorobenzhydryl biguanide; 4-chlorobenzhdrylguanylurea; N-3-lauroxypropyl-$N^5$-p-chlorobenzylbiguanide; 1,6-di-p-chlorophenyl-biguanidohexane; 1,6-bis(2-ethylhexlbiguanido) hexane; 1-(lauryldimethylammonium)-8-(p-chlorobenzyl-dimethylammonium) octane dichloride; 5,6-dichloro-2-guanidinobenzimidazole; $N^1$-p-chlorophenyl-$N^5$-laurylbiguanide; 5-amino-1,3-bis(2-ethylhexyl)-5-methylhexahydro pyrimidine; and their non-toxic acid addition salts. Still in the broader aspects of the invention the pH of the toothpaste may be adjusted as desired, as by inclusion of appropriate amounts of acidic materials (e.g. benzoic acid, citric acid or aluminium sulphate. Generally the toothpaste pH will be in the range of about 5 to 9, determined directly on the paste, preferably about 6 to 8, such as about 6.0, 6.5, 7.0 etc.

Other dentifrice ingredients may also be present if desired, in appropriate conventional proportions. For disclosures of such ingredients and of proportions of ingredients employed in toothpastes, see British patent specifications Nos. 1,249,742, 1,188,353 and 1,260,332.

It is understood that in accordance with generic aspects of this invention, additional dentally acceptable polishing materials may be ground with a surface-modifying agent as described in order to increase their stability characteristics in toothpastes and containers therefor. Thus, the foregoing specific examples are typical, but should not be taken as limitations on the invention.

In this application all proportions are by weight unless otherwise indicated. In the Examples room temperature is employed unless otherwise indicated.

What is claimed is:

1. A toothpaste characterized in that the toothpaste contains abrasive particles of milled alpha-alumina trihydrate, alkali metal monofluorophosphate and alkali metal fluoride, the mol ratio of said monofluorophosphate to said alkali metal fluoride being about 1.5:1 to 5:1 the total amount of said monofluorophosphate and fluoride corresponding to about 500 to 1500 ppm F, and said alpha-alumina trihydrate being reactive with said alkali metal fluoride.

2. A toothpaste as in claim 1 in which the average particle size of milled alpha-alumina trihydrate is about 2 to 15 microns.

3. A toothpaste as in claim 2 in which said total amount is at least about 800 ppm F.

4. A toothpaste as in claim 3 in which said mol ratio is about 1.5:1 to 1.3:1.

5. A toothpaste as in claim 4 in which said alkali metal monofluorophosphate is sodium monofluorophosphate and said alkali metal fluoride is sodium fluoride.

* * * * *